(12) United States Patent
Flamand et al.

(10) Patent No.: US 7,914,800 B2
(45) Date of Patent: Mar. 29, 2011

(54) LTB$_4$ AS VACCINE ADJUVANT

(75) Inventors: Louis Flamand, Sainte-Foy (CA); Jean Gosselin, Cap Rouge (CA); Pierre Borgeat, Sillery (CA)

(73) Assignee: LTB4 Sweden AB, Stockholm (SE)

( * ) Notice: Subject to any disclaimer, the term of this patent is extended or adjusted under 35 U.S.C. 154(b) by 390 days.

(21) Appl. No.: 10/482,393

(22) PCT Filed: Jun. 26, 2002

(86) PCT No.: PCT/CA02/00955
§ 371 (c)(1),
(2), (4) Date: Jun. 9, 2004

(87) PCT Pub. No.: WO03/004054
PCT Pub. Date: Jan. 16, 2003

(65) Prior Publication Data
US 2004/0208882 A1 Oct. 21, 2004

Related U.S. Application Data

(60) Provisional application No. 60/302,705, filed on Jul. 5, 2001.

(51) Int. Cl.
*A61A 45/00* (2006.01)
*A61A 31/20* (2006.01)
*C07C 69/587* (2006.01)
(52) U.S. Cl. .................. 424/278.1; 514/560; 560/128
(58) Field of Classification Search ............... 424/278.1, 424/85.7; 514/560, 46, 50, 263.35
See application file for complete search history.

(56) References Cited

U.S. PATENT DOCUMENTS 5,919,480 A * 7/1999 Kedar et al. ............. 424/450
6,093,741 A * 7/2000 Gosselin et al. ............. 514/560

FOREIGN PATENT DOCUMENTS
WO WO 97/29751 8/1997

OTHER PUBLICATIONS

Yamaoka et al. Leukotriene B4 enhances activation, proliferation, and differentiation of human B lymphocytes. Journal of Immunology. Sep. 15, 1989, vol. 143, No. 6, 1996-2000.*
K. A. Yamaoka et al., "Leukotriene B-4 Enhances Activation Proliferation and Differentiation of Human B Lymphocytes" Journal of Immunology, vol. 143, No. 6 (1989) p. 1996-2000, XP002210600.
S. Yamamoto et al. "Intraperitoneal administration of leukotriene B-4 (LTB-4) and omega-guanidino captoic acid methanesulfonate (GCA) increased the survival of mice challenged with methicillin-resistant staphylococcus aureus (MRSA)." Prostaglandins, vol. 45, No. 6 (1993) pp. 527-534 XP002210601.
H. Claesson et al. "Leukotriene B-4 in the Immune System" International Journal of Immunopharmacology, vol. 14, No. 3 (1992) pp. 441-449, XP002210602.
L. Gagnon et al., "Augmentation of Human Natural Cytotoxic Cell Activity by Leukotriene B4 mediated by enhanced effector-target cell binding and increased lytic efficiency" Cellular Immunology, Academic Press, vol. 110, No. 2, Dec. 1, 1987 pp. 243-252, XP000673615.
M. Rola-Pleszczynski et al., "LEukotriene B4 Augments Human Natural Cytotoxic Cell Activity" Biochemical and Biophysical Research Communications, Academic Press, San Diego, CA, US, vol. 113, No. 2 Jun. 15, 1983 pp. 531-537, XP000673613.
International Search Repprt dated Sep. 5, 2002.

* cited by examiner

*Primary Examiner* — Bo Peng
(74) *Attorney, Agent, or Firm* — Crowell & Moring LLP

(57) ABSTRACT

The present invention relates to a vaccine adjuvant for enhancing immune response of an individual to a vaccine, which comprises an immune-enhancing effective amount of an LTB4 agent in association with a pharmaceutically effective vaccine carrier.

4 Claims, 3 Drawing Sheets

LTB₄ AS VACCINE ADJUVANT

BACKGROUND OF THE INVENTION (a) Field of the Invention

The invention relates to the use of a leukotriene B4 (LTB$_4$) agent as an adjuvant to vaccine preparations.

(b) Description of Prior Art

Vaccines have been used for decades for the prevention of diseases in humans. The efficacy of any vaccine preparation largely depends on its immunogenicity, i.e., their ability to induce strong humoral and cellular immunity. However, many vaccines currently in use have moderate efficacy due to their weak immunogenicity. Because of this, several attempts have been made to supplement vaccine preparations with adjuvants in order to increase the ability of a given vaccine to induce a strong immunity. Unfortunately, most of the substance used as adjuvants have undesirable side effects, which prevent their use in humans.

Adjuvants have been used extensively to improve the generation of an immune response following immunization with a particular antigen, especially in laboratory animals. However, classical and effective adjuvants, such as the Freund's adjuvant, cause undesirable side effects, which prevent their use in humans. Less toxic adjuvants, such as aluminum hydroxide (alum), although relatively well tolerated, do not offer the same degree of immunopotentiation as the Freund's adjuvant.

Thus, because of a lack of effective adjuvant, vaccines for human use are often poorly immunogenic and multiple immunization regimens are required to achieve proper protection against a given pathogen. In addition, long-lasting immunity is often lost in absence of repeated immunization. Intense efforts are therefore devoted to the identification of new effective adjuvants to complement currently used vaccines.

Leukotriene B4 (LTB$_4$) is a known natural molecule. LTB$_4$ is a metabolite of arachidonic acid derived from the 5-lipoxygenase pathway. LTB$_4$ has many reported biological properties. In particular, LTB$_4$ is considered as a potent pro-inflammatory compound; its most important biological activity is its chemotactic and chemokinetic effects on leukocytes. Indeed, LTB$_4$ has been shown to be a potent chemoattractant for human polymorphonuclear leukocytes, monocytes and macrophages, both in vitro and in vivo. LTB$_4$ also activates other leukocyte functions such as degranulation and superoxide anion synthesis. Because of these pro-inflammatory effects, LTB$_4$ is considered as a putative component in defense mechanisms. Moreover, LTB$_4$ is synthesized by inflammatory cells such as polymorphonuclear leukocytes, monocytes and macrophages and is also synthetized by B lymphocytes.

The effects of LTB$_4$ on B cell activity have been previously studied under in vitro experimental conditions. B lymphocyte proliferation, expression of activation markers such as CD23 and immunoglobulin secretion were evaluated. Most studies reached similar conclusions stating that LTB$_4$ by itself, in absence of exogenous cytokines or stimuli (Protein A or *S. aureus*), had no effects on B cell proliferation or immunoflobulin synthesis (IgG or IBM) (Yamaoka, K. A., et al., 1989, *J. Immunol.* 143: 1996-2000; Dugas, B., et al., 1990, *J. Immunol.* 145:3406-3411; Odlander, B., et al., 1989, *Int. J. Tiss. Reac.* XI(6):277-289). The only observable effects of LTB$_4$ on B lymphocytes were recorded when combined to a stimulating agents (Protein A or *S. aureus*) and cytokines. A conflicting paper also reports that LTB$_4$ had an inhibitory effects on the synthesis of immunoglobulin from B lymphocytes (Rola-Plecszczynski, M., et al., 1982, *Biochem. Biophys. Res. Commun.* 108:1531-1537). It thus appear that LTB$_4$ by itself does not stimulate B cell functions and perhaps may even negatively influence it under defined experimental conditions.

It would be highly desirable to be provided with an adjuvant with greater efficacy than the currently used hydroxide aluminum based adjuvant and which would not present the undesirable side effects of the more potent Freund's adjuvant.

SUMMARY OF THE INVENTION

The present invention provides a mean of enhancing immune response, particularly humoral immune response, by concomitant administration of an immune-enhancing effective amount of a LTB$_4$ agent to vaccine preparations.

One aim of the present invention is to provide an adjuvant and use thereof to current and future vaccine preparations allowing them to be more effective in generating protective immunity against pathogens.

Another aim is to provide an adjuvant to vaccine preparations destined to immunosuppressed individuals.

In accordance with the present invention there is provided the use of an LTB$_4$ agent as an adjuvant, for example, with vaccines against the Flu (Influenza) and Tuberculosis (BCG), among others.

In accordance with the present invention there is provided a vaccine adjuvant for enhancing immune response of an individual to a vaccine, which comprises an immune-enhancing effective amount of an LTB$_4$ agent in association with a pharmaceutically effective vaccine carrier.

In accordance with the present invention there is provided a vaccine preparation causing enhanced immune response from an individual, which comprises an immune-enhancing effective amount of an LTB$_4$ agent in association with a vaccine preparation.

In accordance with the present invention there is provided the use of an immune-enhancing effective amount of an LTB$_4$ agent for the preparation of a vaccine causing enhanced immune response from an individual, which comprises an immune-enhancing effective amount of an LTB$_4$ agent in association with a vaccine preparation.

More preferably, the immune response, enhanced by the vaccine of the present invention, is a humoral immune response.

More preferably, the vaccine of the present invention is immunoprotective against a pathogen selected from the group consisting of Influenza and Tuberculosis.

DETAILED DESCRIPTION OF THE INVENTION i) LTB$_4$

Figure 1:
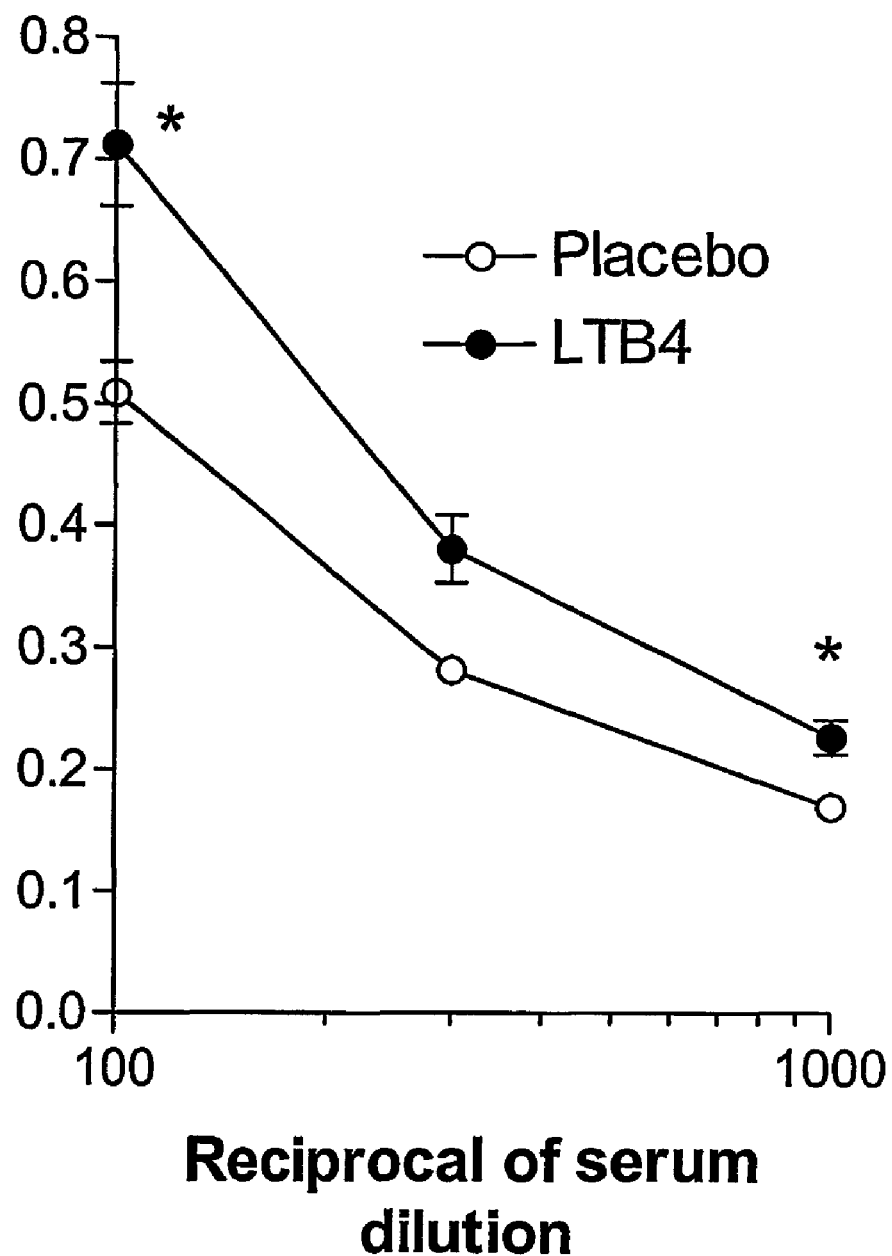
FIG. 1 illustrates the effects of concomitant administration of LTB$_4$ to the Fluviral vaccine on anti-Influenza antibody generation in BALB/c mice.

The term "leukotriene B4 (LTB$_4$) agent" in accordance with the present invention is intended to mean LTB$_4$ or certain structurally related polyunsaturated fatty acids, or substances structurally unrelated to fatty acids, which stimulate the synthesis of $LTB_4$ or other $LTB_4$ agents by cells, or mimic their biological activity. They are either natural substances or analogs of such natural substances. All of the $LTB_4$ agents can be obtained by chemical synthesis by methods described in the literature and most are commercially available.

As used herein, the term "$LTB_4$ agent" is intended to mean one or more of the following polyunsaturated fatty acids, which in addition to $LTB_4$ itself, are analogs of $LTB_4$, or precursors or metabolites of $LTB_4$ or $LTB_4$ analogs: $LTB_4$, 14,15-dihydro-$LTB_4$, 17,18-dehydro-$LTB_4$, 19-hydroxy-$LTB_4$, 20-hydroxy-$LTB_4$ and their 5(R)-hydroxy, 5-keto, 5(S) hydroperoxy, 5(R)-hydroperoxy and 5-deoxy analogs; $LTA_4$; 14,15-dihydro-$LTA_4$, 17,18-dehydro-$LTA_4$; 5(S)-hydroxy-6,8,11,14(E,Z,Z,Z)-eicosatetraenoic acid ("5-HETE"), 14,15-dihydro-5-HETE, 17,18-dehydro-5-HETE, and their 5(R)-hydroxy, 5-keto, 5(S)-hydroperoxy, 5(R)-hydroperoxy analogs; 12(R)-hydroxy-5,8,10,14(Z,Z,E,Z)-eicosatetraenoic acid ("12-HETE"), 5,6-dihydro-12-HETE, 14,15-dihydro-12-HETE, 17,18-dehydro-12-HETE and their 12(S)-hydroxy, 12-keto, 12(S)-hydroperoxy and 12(R)-hydroperoxy analogs and 12-oxo-5,8,10(Z,Z,E)-dodecatrienoic acid, 15(S)-hydroxy-5,8,11,13(Z,Z,Z,E)-eicosatetraenoic acid ("15-HETE"), 5,6-dihydro-15-HETE, 17,18-dehydro-15-HETE and their 15(R)-hydroxy, 15-keto, 15(S)-hydroperoxy, and 15(R)-hydroperoxy analogs.

The term $LTB_4$ agent also includes other derivatives of polyunsaturated fatty acids; some are derived from the cyclooxygenase pathways, the lipoxygenase pathways (5-, 12- and 15-lipoxygenases) or the cytochrome P450 pathways; others are isomers, analogs or derivatives of naturally formed compounds: 12(S)-hydroxy-5,8,10(Z,E,E)-heptadecatrienoic acid; leukotrienes $C_4$, $D_4$ and $E_4$ and their 14,15-dihydro or 17,18-dehydro analogs; N-acyl or N-alkyl derivatives of leukotrienes $C_4$, $D_4$ and $E_4$, and their 14,15-dihydro or 17,18-dehydro analogs; all isomeric 5,12-dihydroxy-6,8,10,14-eicosatetraenoic acids and their 14,15-dihydro or 17,18-dehydro analogs; all isomeric 5,6-dihydroxy-7,9,11,14-eicosatetraenoic acids and their 14,15-dihydro or 17,18-dehydro analogs; all isomeric 5,15-dihydroxy-6,8,11,13-eicosatetraenoic acids (including 5(S),15(S)-dihydroxy-6,8,11,13(E,Z,Z,E)-eicosatetraenoic acid) and their 17,18-dehydro analogs; all isomeric 8-hydroxy-11(12)-epoxy-5,9,14-eicosatrienoic acids (including hepoxilin $A_3$) and their 5,6-dihydro or 14,15-dihydro or 17,18-dehydro analogs; all isomeric 10-hydroxy-11(12)-epoxy-5,8,14-eicosatrienoic acids (including hepoxilin $B_3$) and their 5,6-dihydro or 14,15-dihydro or 17,18-dehydro analogs; all isomeric 8,11,12-trihydroxy-5,9,14-eicosatrienoic acids (including trioxilin $A_3$) and their 5,6-dihydro or 14,15-dihydro or 17,18-dehydro analogs; all isomeric 10,11,12-trihydroxy-5,8,14-eicosatrienoic acids (including trioxilin $B_3$) and their 5,6-dihydro or 14,15-dihydro or 17,18-dehydro analogs; all isomeric 11(12)-epoxy-5,7,9,14-eicosatetraenoic acids and their 14,15-dihydro or 17,18-dehydro analogs; all isomeric 11,12-dihydroxy-5,7,9,14-eicosatetraenoic acids and their 14,15-dihydro or 17,18-dehydro analogs; all isomeric 8(9)-epoxy-5,10,12,14-eicosatetraenoic acids and their 5,6-dihydro or 17,18-dehydro analogs; all isomeric 8,9-dihydroxy-5,10,12,14-eicosatetraenoic acids and their 5,6-dihydro or 17,18-dehydro analogs; all isomeric 8,15-dihydroxy-5,9,11,13-eicosatetraenoic acids and their 5,6-dihydro or 17,18-dehydro analogs; all isomeric 14(15)-epoxy-5,8,10,12-eicosatetraenoic acids and their 5,6-dihydro or 17,18-dehydro analogs; all isomeric 14,15-dihydroxy-5,8,10,12-eicosatetraenoic acids and their 5,6-dihydro or 17,18-dehydro analogs; all isomeric 5-hydroxy-14(15)-epoxy-6,8,10,12-eicosatetraenoic acids and their 17,18-dehydro analogs; all isomeric 5,14,15-trihydroxy-6,8,10,12-eicosatetraenoic acids (including lipoxin $B_4$) and their 17,18-dehydro analogs; all isomeric 5,6,15-trihydroxy-7,9,11,13-eicosatetraenoic acids (including lipoxin $A_4$) and their 17,18-dehydro analogs; all isomeric 5(6)-epoxy-15-hydroxy-7,9,11,13-eicosatetraenoic acids and their 17,18-dehydro analogs; all isomeric 5-hydroxy-6,8,11,14-eicosatetraenoic acids and their 14,15-dihydro or 17,18-dehydro analogs; all isomeric 8-hydroxy-5,9,11,14-eicosatetraenoic acids and their 5,6-dihydro or 14,15-dihydro or 17,18-dehydro analogs; all isomeric 9-hydroxy-5,7,11,14-eicosatetraenoic acids and their 14,15-dihydro or 17,18-dehydro analogs; all isomeric 11-hydroxy-5,8,12,14-eicosatetraenoic acids and their 5,6-dihydro or 17,18-dehydro analogs; all isomeric 12-hydroxy-5,8,10,14-eicosatetraenoic acids and their 5,6-dihydro or 14,15-dihydro or 17,18-dehydro analogs; all isomeric 15-hydroxy-5,8,11,13-eicosatetraenoic acid and their 5,6-dihydro or 17,18-dehydro analogs; all isomeric 9-hydroxy-10,12-octadecadienoic acids; all isomeric 13-hydroxy-9,11-octadecadienoic acids; 12(R)-hydroxy-5,8,14(Z,Z,Z)-eicosatrienoic acid; all isomeric 5(6) oxido- or 5,6-dihydroxy-8,11,14-eicosatrienoic acids and their 14,15-dihydro or 17,18-dehydro analogs; all isomeric 8(9)-oxido- or 8,9-dihydroxy-5,11,14-eicosatrienoic acids and their 5,6-dihydro or 14,15-dihydro or 17,18-dehydro analogs; all isomeric 11(12)-oxido- or 11,12-dihydroxy-5,8,14-eicosatrienoic acids and their 5,6-dihydro or 14,15-dihydro or 17,18-dehydro analogs; all isomeric 14(15)-oxido- or 14,15-dihydroxy-5,8,11-eicosatrienoic acids and their 5,6-dihydro or 17,18-dehydro analogs.

The term $LTB_4$ also includes variants which are non-covalently modified fatty acids such as the sodium or the potassium salts of the $LTB_4$ agents.

The term $LTB_4$ agent also includes variants where a modification is introduced into the molecule by reacting targeted functional groups of the fatty acid with an organic derivatizing agent that is capable of reacting with the selected functional group (yielding for example, ester and ether derivatives of $LTB_4$ agent) or to cause intramolecular rearrangement (such as the formation of lactones with hydroxylated fatty acids). The resulting compounds may have altered biological activity and/or bioavailability. Thus, the covalently modified fatty acid can be a pro-drug with reduced biological activity which upon in vivo administration is slowly transformed into a more active molecule (underivatized $LTB_4$ agent). Variants may also be metabolically stable and biologically active analogs of $LTB_4$ agents altered in a way that will result in retarded disposition of the compound (decreased metabolism and/or elimination). Variants with modifications at the omega end (such as 20,20,20-trifluoromethyl-$LTB_4$) show increased resistance to omega-oxidation (a catabolic process of unsaturated fatty acids); other variants with modification at the omega end at the level of carbons 13 to 20 (such as 19-methyl-$LTB_4$ or 19,19-dimethyl-$LTB_4$ or 19-fluoro-$LTB_4$ or 19,19-difluoro-$LTB_4$ or 18,20-difluoro-$LTB_4$ or 20-fluoro-$LTB_4$) may show increased resistance to omega-oxidation and variants with modifications at the carboxylic end, at the level of carbon 1, 2, 3 or 4 (for example, 3-thio-$LTB_4$, 3-hydroxy-$LTB_4$, 3-methyl-$LTB_4$ or 3,3-dimethyl-$LTB_4$ or 3-fluoro-$LTB_4$ or 3,3-difluoro-$LTB_4$ or 2,3-difluoro-$LTB_4$, $LTB_4$ methylsulfonylamide, $LTB_4$ methylamide), may show increased metabolic resistance to beta-oxidation and/or to elimination (such as uptake by probenecide-sensitive organic acid transporter). Other variants with modification(s) at carbon 12, such as 12(R)-methyl-$LTB_4$, may show increased resistance to reduction of the 11,12 double bond (a metabolic pathway of $LTB_4$). Other variants are analogs of $LTB_4$ agents with structural changes, such as changes in chain length (chain length increased or decreased by up to 4 carbons), addition of double bond(s), saturation of double bond(s), changes in double bond(s) geometry (cis to trans or vice versa), change of double bond(s) for triple bond(s), change in the configuration of one or several functional group(s) (R to S or S to R), or where one or several functional group(s) or substituent(s) are either removed, added or changed for other functional groups or substituents (including but not limited to hydroperoxyl, carbonyl, sulfhydryl, sulfoxide, sulfone, cysteinyl, glutathionyl, cysteinyl-glycine, methyl, isopropyl, benzyl, chloro, fluoro), or where the positions of one or several functional groups and/or one or several double bonds has been moved by one, two or three carbons relative to the omega end. The $LTB_4$ agent may be a variant carrying one or several of the above mentioned structural modifications.

The $LTB_4$ agents and variants of $LTB_4$ agents are structurally related to $LTB_4$ and bind or may bind with different affinities to either the cell surface binding sites of $LTB_4$ (or other related eicosanoids, including but not limited to 5-HETE, $LTD_4$, lipoxin $A_4$) present on various leukocytes (and other cell types), or to the nuclear binding site of $LTB_4$, the transcription factor PPARα (peroxisome proliferator-activated receptor alpha) (Devchand P. R., et al., Nature 384:39, 1996), or to other unknown binding sites of $LTB_4$, resulting in the expression of the biological activities of $LTB_4$ and $LTB_4$ agents. The $LTB_4$ agents and variants show or may show biological activities qualitatively similar to that of $LTB_4$ (but may be more or less active than $LTB_4$ itself) and thus can be expected to exert an adjuvant activity similar to that of $LTB_4$. The $LTB_4$ agents and variants thereof are included within the scope of this invention.

The term $LTB_4$ agent also includes agents not structurally related to $LTB_4$ including but not limited to the chemotactic peptide formyl-met-leu-phe (fMLP) (and analogs such as N-formyl-nle-leu-phe, N-formyl-met-leu-phe-benzylamide, N-formyl-met-leu-phe-methyl-ester and N-formyl-Nle-leu-phe-nle-tyr-lys), the complement fragment C5a and analogs, and the biologically active phospholipid platelet-activating factor, 1-0-hexadecyl-2-0-acetyl-sn-glycero-3-phospho-choline (and analogs such as 1-0-octadecyl-2-0-sn-glycero-3-phosphocholine and 1-0-hexadecyl-2-N-methyl-carbamyl-sn-glycero-3-phosphocholine) that stimulate or may stimulate the release of unsaturated fatty acids in cells (mainly arachidonic acid) and consequently the formation of one or several $LTB_4$ agents, and may therefore exhibit an adjuvant activity similar to that of $LTB_4$. The above-mentioned $LTB_4$ agents not structurally related to $LTB_4$ are thus included within the scope of this invention.

The term $LTB_4$ agent also includes formulations of compounds which might contain a mixture of two or several $LTB_4$ agents or an $LTB_4$ agent and one or several equally or less active isomer(s) of the $LTB_4$ agent (positional, geometrical or optical isomers).

The term $LTB_4$ agent also includes antibodies to the $LTB_4$ receptor, or anti-idiotypic antibodies to antibodies raised against $LTB_4$ or one of the above-mentioned analogs or variants of $LTB_4$, which can be expected to elicit an $LTB_4$-like biological response, such as an antiviral effect.

ii) Vaccines

The vaccines for which $LTB_4$ can be used as an adjuvant include all vaccines available for humans and animals. The expression "vaccine" is intended to include any types of preparations (purified or recombinant proteins, whole-inactivated microorganisms, fragmented microorganisms, live-attenuated microorganisms, complex sugars, etc). The expression "microorganisms" includes DNA and RNA viruses, retroviruses, bacteria, parasites and fungi.

To test the adjuvant potential of $LTB_4$, groups of 10 BALB/c mice were immunized once by intramuscular injection with 5 μl of the commercial "Fluviral" vaccine preparation in combination with saline or 1 ng of $LTB_4$. Fourteen days following immunization, mice were bled and sera analyzed for specific anti-Influenza IgG antibodies by ELISA. The results obtained indicate that mice that received $LTB_4$ concomitantly with the vaccine developed a greater anti-Influenza antibody response (*$p<0.05$) in all of the three dilutions tested. A dose of 1 ng of $LTB_4$ was found to be optimal. These results clearly show that a simple addition of $LTB_4$ to the vaccine preparation can positively influence specific antibody production.

Another vaccine preparation that would greatly benefit from an adjuvant is the BCG vaccine against tuberculosis. This live attenuated vaccine from Pasteur-Merieux Connaught is weakly immunogenic requiring multiple administrations in order to induce anti-BCG antibodies. We tested whether $LTB_4$ could influence anti-BCG antibody development. BALB/c mice (n=4-5/group) were immunized intradermally four times with the vaccine preparation in combination or not with varying doses of $LTB_4$ (1-10 ng). Mice were immunized on day 0, 24, 68 and 145. On day 160, mice were bled and sera analyzed for anti-BCG antibodies by ELISA. The results indicate that sera from $LTB_4$ treated mice had higher levels of anti-BCG antibodies than the BCG+saline group, over all dilutions of sera tested. These results clearly show that a weak vaccine, such as the BCG vaccine, can greatly benefit from the adjuvant properties of $LTB_4$, making it more efficient at inducing a specific antibody response.

Our next series of experiments were designed to test the potential of $LTB_4$ to modulate antibody response during an acute CMV infection. BALB/c mice were infected by intraperitoneal (i.p.) injection with 10,000 pfu of murine CMV. On day 5 post-infection, mice (n=10) received saline by i.p. injection or $LTB_4$ (5 μg/kg) (n=9) by i.p. injection 3 times a week for 12 weeks. At that time, sera was taken from each mouse and tested for anti-CMV specific antibodies. The results obtained indicate that mice receiving $LTB_4$ had more anti-CMV antibodies than mice from the placebo-treated group indicating that $LTB_4$ can positively influenced anti-CMV antibody formation.

Lastly, the sera from each mouse infected with CMV and treated with saline or $LTB_4$ (see above) were analyzed for neutralizing antibodies. Briefly, a 1/100 dilution of individual serum was incubated with 175 pfu of murine CMV for 1 hour on ice. Samples (sera-virus) were then added to mouse embryonic fibroblast and incubated at 37° C. for 2 hour. Unadsorbed viruses were removed and cells were overlaid with methyl cellulose and incubated for 4 days at 37° C. in a humidified atmosphere with 5% $CO_2$. At this time cells were fixed, colored with violet crystal and the number of plaques (CMV infected foci) counted. A reduction in plaque number indicates that a serum has neutralizing activity. Uninfected mice had no neutralizing antibodies against CMV, as expected. Two out of 10 mice (20%) treated with a placebo were found to possess sera with CMV neutralizing activity. This is in sharp contrast with 78% of sera of $LTB_4$ treated-mice, which showed CMV neutralizing activity. We next compared the neutralizing activity of sera that tested positive for CMV neutralization. The 2 sera of infected mice that received saline were able to reduce, in average, CMV infectivity by 24%. In contrast, the 7 sera of $LTB_4$ treated-mice were found capable of reducing CMV infectivity by 45%, almost twice the activity of control mice.

The present invention will be more readily understood by referring to the following examples which are given to illustrate the invention rather than to limit its scope.

Example I

Assay for Anti-Influenza Antibody Generation in BALB/c Mice Following Immunization With the "Fluviral" Vaccine Adult (6-8 weeks) BALB/c female mice were immunized by intramuscular injection with 5 µl of the commercial Influenza (Fluviral) vaccine in combination or not with 1 ng of $LIB_4$. Fourteen days later, mice were bled by cardiac puncture and sera obtained. Anti-Influenza antibodies were quantitated by enzyme-linked immunosorbent assay (ELISA). Wells of a 96-well plate were coated with the Fluvial vaccine preparation (1/100 dilution) in 0.1 M carbonate buffer (pH 9.0) by overnight incubation at 4° C. Wells were washed with Trisbuffered saline with 0.1% Tween-20 (TBS-T) followed by the addition of 100 µl of increasing dilutions of the sera to be tested. After a 2-hour incubation at room temperature, the wells were washed six times with TBS-T. One hundred µl of alkaline-labeled goat anti-mouse IgG were added to each well and incubation allowed to proceed for one hour at room temperature. Wells were washed six more times with TBS-T followed by the addition of OPD substrate and developer solution. After 30 minutes, the absorbance (405 nm) from each well was recorded using an ELISA plate reader. The values, expressed as optical density (OD), were plotted against the reciprocal of serum dilution. Results show the mean OD of sera from 5 animals per group+S.D. in one experiment representative of two (2) other. As shown in FIG. 1, mice receiving a combination of vaccine and 1 ng of $LTB_4$ generated a significantly higher anti-Influenza antibody response when compared to the mice receiving the vaccine and saline.

Example II

Figure 2:
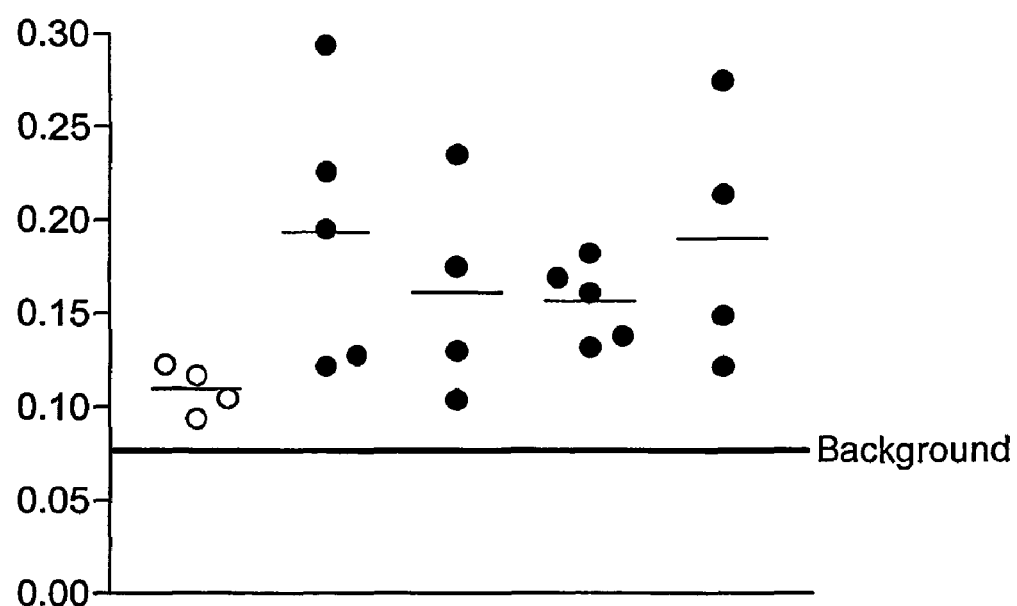
FIG. 2 illustrates the effects of concomitant admistration of LTB$_4$ to the BCG vaccine on anti-mycobacterium tuberculosis antibody generation in BALB/c mice.

Assay for Anti-Mycobacterium Tuberculosis Antibody Generation in BALB/c Mice Following Immunization With the BCG Vaccine Adult (6-8 weeks) female BALB/c mice were immunized by intradermal injections with 25 µl of the anti-tuberculosis BCG vaccine in combination or not with varying doses (1-10 ng) of $LTB_4$. In all cases, the injected volumes were brought up to 100 µl with saline. Mice were immunized on days 0, 24, 68 and 145. On day 160, mice were bled by cardiac punctures and sera tested for anti-mycobacterium tuberculosis antibodies. ELISA plates were coated with 1/50 dilution of the BCG vaccine preparation in 0.1 M carbonate buffer (pH 9.0) by overnight incubation at 4° C. Wells were washed with TBS-T and non-specific sites were blocked by the addition of saline containing 10% fetal bovine serum for one hour at room temperature. After several washes, 100 µl of increasing dilutions of the sera to be tested were added to each well. As a negative control (background), the serum of a naïve BALB/c mouse was used. After a 2-hour incubation at room temperature, the wells were washed six times with TBS-T. One hundred µl of alkaline-labeled goat anti-mouse IgG were added to each well and incubation allowed to proceed for one hour at room temperature. Wells were washed six more times-with TBS-T followed by the addition of OPD substrate and developer solution. After 30 minutes, the absorbance (405 nm) from each well was recorded using an ELISA plate reader. The values, expressed as optical density (OD), were plotted against the reciprocal of serum dilution. Results (FIG. 2) show the mean OD of each group of serum. In average, sera of mice receiving a combination of BCG vaccine and $LTB_4$ had greater reactivity against mycobacterium antigens than the group receiving BCG+saline, indicating a higher specific antibody response.

Example III

Figure 3:
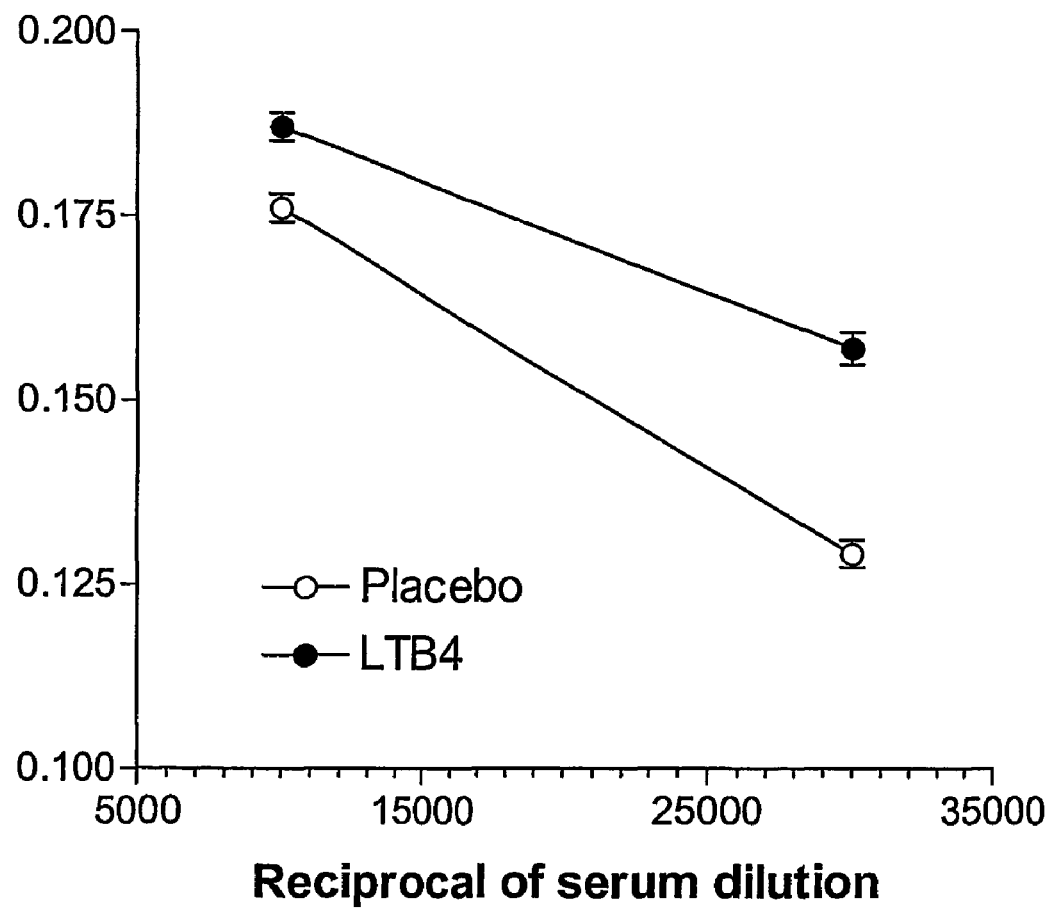
FIG. 3 illustrates the effects of prolonged LTB$_4$ administration on anti-cytomegalovirus (CMV) antibody generation during acute CMV infection in BALB/c mice.

Assay for Anti-CMV Antibody Generation Following Acute CMV Infection in BALB/c Mice Total Anti-CMV Antibodies Adult (6-8 weeks) female BALB/c mice were infected by intraperitoneal (I.P.) injection with $1 \times 10^4$ pfa of murine CMV. Starting on the fifth day post-infection, mice were injected with saline or $LTB_4$ (5 µg/kg) by I.P. injection at a frequency of three times a week for 12 weeks. Mice were then bled and sacrificed. Total anti-CMV antibodies from each mouse were quantified by ELISA. ELISA plates were coated with a lysates from CMV-infected fibroblasts as the source of CMV antigens. One µg of protein lysates were added to each well and incubated-overnight at 4° C. After several washes with TBS-T, non-specific sites were blocked by the addition of saline containing 10% fetal bovine serum for one hour at room temperature. Wells were rinsed 3 times with TBS-T and reacted with diluted sera preparations from each mouse. Sera were allowed to react for 2 hours at room temperature with the serum of a naïve (uninfected) BALB/c mouse used as negative control. After a 2-hour incubation at room temperature, the wells were washed six times with TBS-T. One hundred µl of alkaline-labeled goat anti-mouse IgG were added to each well and incubation allowed to proceed for one hour at room temperature. Wells were washed six more times with TBS-T followed by the addition of OPD substrate and developer solution. After 30 minutes, the absorbance (405 nm) from each well was recorded using an ELISA plate reader. The values, expressed as optical density (OD), were plotted against the reciprocal of serum dilution. Results (FIG. 3) represent the mean and standard error derived from 9 data points for each group. The results obtained indicate that mice receiving $LTB_4$ had more anti-CMV antibodies than mice from the saline-treated group indicating that $LTB_4$ can positively influenced anti-CMV antibody formation.

Neutralizing CMV Antibodies

The serum from each mouse, described above, were tested for their CMV neutralizing activity. Briefly, a 1/100 dilution of individual serum was incubated with 175 pfu of murine CMV for 1 hour on ice. Samples (sera-virus) were then added to mouse embryonic fibroblast and incubated at 37° C. for 2 hour. Unadsorbed viruses were removed and cells were overlaid with methyl cellulose and incubated for 4 days at 37° C. in a humidified atmosphere with 5% $CO_2$. At this time cells were fixed, colored with violet crystal and the number of plaques (CMV infected foci) counted. A reduction in plaque number indicates that a serum has neutralizing activity. Uninfected mice had no neutralizing antibodies against CMV, as expected (Table 1). Table 1 illustrates the effects of prolonged $LTB_4$ administration on neutralizing anti-CMV antibody generation during acute CMV infection in BALB/c mice.

TABLE 1

Effects of LTB$_4$ administration of the generation of CMV neutralizing antibodies

|  | Mice sera with CMV-neutralizing activity (%) |
| --- | --- |
| Naïve (uninfected) | 0/10 (0%) |
| Placebo | 2/10 (20%) |
| LTB$_4$ | 7/9 (78%) |

Two out of 10 mice (20%) treated with saline were found to possess sera with CMV neutralizing activity at a 1/100 dilution. This is in sharp contrast with 78% (7/9) of sera from LTB$_4$ treated-mice, which showed CMV neutralizing activity (Table 1). We next compared the neutralizing activity of sera that tested positive for CMV neutralization. The 2 sera of saline treated-mice were able to reduce, in average, CMV infectivity by 24%. In contrast, the 7 sera of LTB$_4$ treated-mice were found capable of reducing CMV infectivity by 45%, almost twice the activity of control mice.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A vaccine preparation for enhancing immune response in an individual, which comprises an immune-enhancing effective amount of an leukotriene B4 (LTB$_4$) agent in association with a vaccine, wherein said LTB$_4$ agent is LTB$_4$ or a salt thereof.

2. The vaccine preparation of claim 1, wherein said vaccine is immunoprotective against a pathogen selected from the group consisting of Influenza and Tuberculosis.

3. The vaccine preparation of claim 1 wherein the salts are the sodium or potassium salts of the LTB$_4$ agent.

4. The vaccine preparation of claim 2 wherein salts are the sodium or potassium salts of the LTB$_4$ agent.

\* \* \* \* \*